(12) United States Patent
Barbour et al.

(10) Patent No.: US 6,504,083 B1
(45) Date of Patent: Jan. 7, 2003

(54) MAIZE GOS-2 PROMOTERS

(75) Inventors: Eric Barbour, Des Moines, IA (US); Terry EuClaire Meyer, Urbandale, IA (US); Mohamed Eid Saad, Giza (EG)

(73) Assignees: Pioneer Hi-Bred International, Inc., Des Moines, IA (US); Agricultural Genetic Engineering Research Institute, Giza (EG)

( * ) Notice: Subject to any disclaimer, the term of this patent is extended or adjusted under 35 U.S.C. 154(b) by 0 days.

(21) Appl. No.: 09/410,935

(22) Filed: Oct. 4, 1999

Related U.S. Application Data

(60) Provisional application No. 60/103,294, filed on Oct. 6, 1998, and provisional application No. 60/107,201, filed on Nov. 5, 1998.

(51) Int. Cl.[7] .......................... A01H 1/00; C07H 21/04; C07K 14/415; C12N 5/14
(52) U.S. Cl. .......................... 800/278; 435/6; 435/410; 435/419; 435/252.3; 435/320.1; 536/23.1; 536/23.6; 536/24.1; 536/24.3; 536/24.33; 800/295
(58) Field of Search .......................... 435/6, 410, 419, 435/252.3, 320.1; 536/23.1, 23.6, 24.1, 24.3, 24.33; 800/278, 295

(56) References Cited

U.S. PATENT DOCUMENTS 5,750,866 A * 5/1998 Dietrich et al.

FOREIGN PATENT DOCUMENTS

| EP | 0 342 926 A2 | 11/1989 |
|---|---|---|
| JP | 61 280283 | 12/1986 |
| WO | WO 91/09948 | 7/1991 |
| WO | WO 91/09948 A1 | 7/1991 |
| WO | WO 95/35386 A | 12/1995 |
| WO | WO 95/35386 A1 | 12/1995 |
| WO | WO 96/07746 A1 | 3/1996 |
| WO | WO 96/07746 A1 | 3/1996 |

OTHER PUBLICATIONS

McElroy et al., Isolation of an Efficient Actin Promoter for Use in Rice Transformation, *The Plant Cell*, Feb. 1990, pp. 163–171, vol. 2, American Society of Plant Physiologists.

Lal et al., Characterization of a Maize cDNA that complements an Enolase–Deficient Mutant of *Escherichia coli*, *Plant Molecular Biology*, 1991, pp. 787–795, vol. 16, Kluwer Academic Publishers, Belgium.

dePater et al., The Promoter of the Rice Gene GOS2 is Active in Various Different Monocot Tissues and Binds Rice Nuclear Factor ASF–1,*The Plant Journal*, 1992, pp. 837–844, vol. 2(6), Netherlands.

An et al. Strong, Constitutive Expression of the Arabidopsis ACT2/ACT8 actine subclass in Vegetative Tissues, *The Plant Journal*, 1996, pp. 107–121, vol. 10(1).

An, Y., et al, Strong, Constitutive Expression of the Arabidopsis ACT2/ACT8 Actin Subclass in Vegative Tissues, The Plant Journal, 1996, vol. 10, No. 1, pp. 107–121.

McElroy D., et al., Isolation of an Efficient Actine Promoter for Use in Rice Transformation, American Society of Plant Physiologists, The Plant Cell, 1990, vol. 2, pp. 163–171.

* cited by examiner

*Primary Examiner*—Phuong T. Bui
(74) *Attorney, Agent, or Firm*—Alston & Bird LLP

(57) ABSTRACT

The invention provides compositions and methods for regulating expression of heterologous nucleotide sequences in a plant. Compositions are nucleotide sequences for tissue-independent or constitutive promoters for genes encoding actin-2, enolase, Gos-2 and L41. A method for expressing a heterologous nucleotide sequence in a plant using the promoter sequences disclosed herein is provided. The method comprises transforming a plant cell with a nucleotide sequence operably linked to one of the promoters of the present invention and regenerating a stably transformed plant from the transformed plant cell.

18 Claims, 6 Drawing Sheets

SEQUENCE LISTING

<160> NUMBER OF SEQ ID NOS: 19

<210> SEQ ID NO 1
<211> LENGTH: 613
<212> TYPE: DNA
<213> ORGANISM: Zea mays
<220> FEATURE:
<221> NAME/KEY: promoter
<222> LOCATION: (0)...(0)
<223> OTHER INFORMATION: Actin-2

<400> SEQUENCE: 1

```
tcagtatgat tgctttcaat ataggctgat ggagcctatg aatgatctat aactatgtga      60
ttggatgtct taacttgcgt agccaagctc gtatgagcct cttttactgg gtaccactaa     120
tttctatata ttagatacag ttaaataagt ctaaattaca tcggtgcgtg cgtgccagta     180
cgactagatg tagtgaacta aacacaggtt aagctgtgat caatgtatgt agagagtctg     240
actctttata tgcggacaac taaacacacg ataagtgtcg agaatgattg aggaaatatt     300
ggtcgttcca cgtgattgag taagaatgag agggaaataa aaggatttgg tgcgttggtt     360
ttgaaggcag gatttggtta ggatgggtgg acgtttgaag tgatgagttt ttcaagcgta     420
```

-continued

```
tagattttct atttgtcctt tttaattaac tttctcccag ccgggatgcg cgtataaaaa      480
ccggcgaaac ccttggctct cctcattcgg cctatcacaa ccgcttactc tcgtgcgctc      540
tccgtgggag cgaggacccg cggccggcgg cagcggcagc ttctcctaga tctccggcat      600
catcagtgga tcc                                                         613
```

<210> SEQ ID NO 2
<211> LENGTH: 664
<212> TYPE: DNA
<213> ORGANISM: Zea mays
<220> FEATURE:
<221> NAME/KEY: promoter
<222> LOCATION: (0)...(0)
<223> OTHER INFORMATION: Enolase

<400> SEQUENCE: 2

```
tcatatattt atgaacggag atagtgcatc tatcatgcga ttcttcgacg gagtcgacgt       60
ctgattggac cagaatttca gatggtgagc aaaagtgcca cttgcctgcc tccttttctc      120
gtgcctgcct aacacgtgcc tttgatctct agggcagtta taattaagac aagcaggtta      180
tattataagt caaggataga aagaaaggag aaacaatata ctatttaaga tcagataaaa      240
aaagagctaa taattttttg ggacacatat actggttaca ttgttataat ctgtatatat      300
cacgttgttc gaatatattc caaattttta ctatgattcg tgctctaccg gaactacttc      360
tagattttga aactttatg agaattttct tatttagata cactaaggct aattttggtt       420 ggttttggc tcgctagcta ccattacctc ctgcatctag acattacaaa tttacaataa       480
ataaagttcc tagattttga acgaaaccag cagagcgcac accgtccttg ccccacggaa      540
caagaaaaat ggaatatgct cccgcagccc tcgtggaaac caagggcgga ccttcccctc      600
ctccaagcaa atccgaggcc cacccacggg ccgctcgaac atctgtcacc gccaagtggg      660
atcc                                                                  664
```

<210> SEQ ID NO 3
<211> LENGTH: 862
<212> TYPE: DNA
<213> ORGANISM: Zea mays
<220> FEATURE:
<221> NAME/KEY: promoter
<222> LOCATION: (0)...(0)
<223> OTHER INFORMATION: Gos-2

<400> SEQUENCE: 3

```
attattggct gtaggattct aaacagagcc taaatagctg gaatagctct atagccctca       60
atccaaacta atgatatcta tacttatgca actctaaatt tttattctaa aagtaatatt      120 tcattttgt caacgagatt ctctactcta ttccacaatc ttttgaagct atatttacct       180
taaatctgta ctctatacca ataatcatat attctattat ttattttat ctctctccta       240 aggagcatcc ccctatgtct gcatggcccc cgcctcgggt cccaatctct tgctctgcta      300
gtagcacaga agaaaacact agaaatgact tgcttgactt agagtatcag ataaacatca      360
tgtttactta actttaattt gtatcggttt ctactatttt tataatattt ttgtctctat      420
agatactacg tgcaacagta taatcaacct tataatattt ttgtctctat agatactacg      480
tgcaacagta taatcaacct acagcgttcc ttttatggtt cctcactggg cacagcataa      540
acgaaccctg tccaatgttt tcggcgcgaa caaacagaaa ttccatcagc gaacaaacaa      600
catacatgcg agatgaaaat aaataataaa aaaagctccg tctcgatagg ccggcacgaa      660
tcgagagcct ccatagccag tttttttccat cggaacggcg gttcgcgcac ctaattatat      720
```

```
gcaccacacg cctataaagc caaccaaccc gtcggagggg cgcaagccag acagaagaca    780
gcccgtcagc ccctctcgtt tttcatccgc cttcgcctcc aaccgcgtgc gctccacgcc    840
tcctccagga aagcgaggat cc                                             862
```

<210> SEQ ID NO 4
<211> LENGTH: 461
<212> TYPE: DNA
<213> ORGANISM: Zea mays
<220> FEATURE:
<221> NAME/KEY: promoter
<222> LOCATION: (0)...(0)
<223> OTHER INFORMATION: L41

<400> SEQUENCE: 4

```
tctgaaccta taaaatttgt tcacatttgt gtttatcaat ccactataca aaagaggatg     60
tagggtataa ctcatgctca aacctttatt aaacacatgt gctagtatct aggctgctcg    120
atgatgttct attgttcgcg actgtgttgt gtgaaaactg cagcagatca actgggccat    180
gctggcctgg ttatgcacgg gcacgctcga agcggaacct agtgagcagc caacagcgt     240 cctagcggta ggcgtacggc ccattagaag tacacggccc gaatccccgg agaaaaccct    300
agacagcggc gggcgccttg ccataaaagc acagcgcttc tacacccgcc gccgccactc    360
gttgcagcct ctctacctct acctactgga gtagggagca cgccgcacga gcccttccg     420 ccgccgccaa aatggtgaac gttcctaaga ccaagggatc c                        461
```

<210> SEQ ID NO 5
<211> LENGTH: 27
<212> TYPE: DNA
<213> ORGANISM: Artificial Sequence
<220> FEATURE:
<223> OTHER INFORMATION: Gene specific primer 1 for Actin-2

<400> SEQUENCE: 5

```
cttggactgg gcctcgtcac caacata                                         27
```

<210> SEQ ID NO 6
<211> LENGTH: 32
<212> TYPE: DNA
<213> ORGANISM: Artificial Sequence
<220> FEATURE:
<223> OTHER INFORMATION: Gene specific primer 1 for Gos-2

<400> SEQUENCE: 6

```
accagcacca gagtcctcag catttgcctc ag                                   32
```

<210> SEQ ID NO 7
<211> LENGTH: 28
<212> TYPE: DNA
<213> ORGANISM: Artificial Sequence
<220> FEATURE:
<223> OTHER INFORMATION: Gene specific primer 1 for Enolase

<400> SEQUENCE: 7

```
tttgcctcgc aagtcacgct cgattcgg                                        28
```

<210> SEQ ID NO 8
<211> LENGTH: 29
<212> TYPE: DNA
<213> ORGANISM: Artificial Sequence
<220> FEATURE:
<223> OTHER INFORMATION: Gene specific primer 1 for L41

<400> SEQUENCE: 8
tttccctggg cagacaggct atccttacc                                           29

<210> SEQ ID NO 9
<211> LENGTH: 28
<212> TYPE: DNA
<213> ORGANISM: Artificial Sequence
<220> FEATURE:
<223> OTHER INFORMATION: Gene specific primer 2 for Actin-2

<400> SEQUENCE: 9
actgatgatg ccggagatct aggagaag                                            28

<210> SEQ ID NO 10
<211> LENGTH: 30
<212> TYPE: DNA
<213> ORGANISM: Artificial Sequence
<220> FEATURE:
<223> OTHER INFORMATION: Gene specific primer 2 for Gos-2

<400> SEQUENCE: 10
tcgctttcct ggaggaggcg tggagcgcac                                          30

<210> SEQ ID NO 11
<211> LENGTH: 27
<212> TYPE: DNA
<213> ORGANISM: Artificial Sequence
<220> FEATURE:
<223> OTHER INFORMATION: Gene specific primer 2 for Enolase

<400> SEQUENCE: 11
ccacttggcg gtgacagatg ttcgagc                                             27

<210> SEQ ID NO 12
<211> LENGTH: 32
<212> TYPE: DNA
<213> ORGANISM: Artificial Sequence
<220> FEATURE:
<223> OTHER INFORMATION: Gene specific primer 2 for L41

<400> SEQUENCE: 12
cttggtctta ggaacgttca ccattttggc gg                                       32

<210> SEQ ID NO 13
<211> LENGTH: 45
<212> TYPE: DNA
<213> ORGANISM: Artificial Sequence
<220> FEATURE:
<223> OTHER INFORMATION: Adapter Primer AP3

<400> SEQUENCE: 13
atatgcatgc atctgcagat cccgggacta tagggcacgc gtggt                         45

<210> SEQ ID NO 14
<211> LENGTH: 45
<212> TYPE: DNA
<213> ORGANISM: Artificial Sequence
<220> FEATURE:
<223> OTHER INFORMATION: Gene specific primer 3 for Acti-2

<400> SEQUENCE: 14
atccatggtg tcgtgtggat ccactgatga tgccggagat ctagg                         45

<210> SEQ ID NO 15
<211> LENGTH: 44

-continued

```
<212> TYPE: DNA
<213> ORGANISM: Artificial Sequence
<220> FEATURE:
<223> OTHER INFORMATION: Gene specific primer 3 for Gos-2

<400> SEQUENCE: 15
atccatggtg tcgtgtggat cctcgctttc ctggaggagg cgtg                    44

<210> SEQ ID NO 16
<211> LENGTH: 44
<212> TYPE: DNA
<213> ORGANISM: Artificial Sequence
<220> FEATURE:
<223> OTHER INFORMATION: Gene specific primer 3 for Enolase

<400> SEQUENCE: 16
atccatggtg tcgtgtggat cccacttggc ggtgacagat gttc                    44

<210> SEQ ID NO 17
<211> LENGTH: 45
<212> TYPE: DNA
<213> ORGANISM: Artificial Sequence
<220> FEATURE:
<223> OTHER INFORMATION: Gene specific primer 3 for L41

<400> SEQUENCE: 17
atccatggtg tcgtgtggat cccttggtct taggaacgtt cacca                   45

<210> SEQ ID NO 18
<211> LENGTH: 22
<212> TYPE: DNA
<213> ORGANISM: Artificial Sequence
<220> FEATURE:
<223> OTHER INFORMATION: Clontech AP1 primer

<400> SEQUENCE: 18
gtaatacgac tcactatagg gc                                            22

<210> SEQ ID NO 19
<211> LENGTH: 19
<212> TYPE: DNA
<213> ORGANISM: Artificial Sequence
<220> FEATURE:
<223> OTHER INFORMATION: Clontech AP2 primer

<400> SEQUENCE: 19
actatagggc acgcgtggt                                                19
```

MAIZE GOS-2 PROMOTERS

CROSS-REFERENCE TO RELATED APPLICATIONS

This application claims the benefit of U.S. Provisional Application No. 60/103,294, filed Oct. 6, 1998 and U.S. Provisional Application No. 60/107,201 filed Nov. 5, 1998.

FEDERALLY SPONSORED RESEARCH OR DEVELOPMENT

This invention was made with Government support under a grant from the United States Agency for International Development (USAID), Grant Number 263-0240-G-00-6014-00. The Government has certain rights to this invention.

FIELD OF THE INVENTION

The present invention relates to the field of plant molecular biology, more particularly to regulation of gene expression in plants.

BACKGROUND OF THE INVENTION

Expression of heterologous DNA sequences in a plant host is dependent upon the presence of an operably linked promoter that is functional within the plant host. Choice of the promoter sequence will determine when and where within the organism the heterologous DNA sequence is expressed. Where expression in specific tissues or organs is desired, tissue-preferred promoters may be used. In contrast, where gene expression in response to a stimulus is desired, inducible promoters are the regulatory element of choice. Where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

Frequently it is desirable to have constitutive or inducible expression of a DNA sequence throughout the cells of an organism in a tissue-independent manner. For example, increased resistance of a plant to infection by soil- and air-borne pathogens might be accomplished by genetic manipulation of the plant's genome to comprise a constitutive promoter operably linked to a heterologous pathogen-resistance gene such that pathogen-resistance proteins are continuously expressed throughout the plant's tissues.

Alternatively, it might be desirable to inhibit expression of a native DNA sequence within a plant's tissues to achieve a desired phenotype. In this case, such inhibition might be accomplished with transformation of the plant to comprise a constitutive, tissue-independent promoter operably linked to an antisense nucleotide sequence, such that constitutive expression of the antisense sequence produces an RNA transcript that interferes with translation of the mRNA of the native DNA sequence.

Currently, only a few promoters that exhibit a constitutive pattern of expression in plants are available, examples of which include the CaMV 35S, nopaline synthase, and the ubiquitin promoters. The increasing interest in cotransforming plants with multiple plant transcription units (PTU) and the potential problems associated with using common regulatory sequences for these purposes merit having a number of such promoter sequences available.

Thus, isolation and characterization of constitutive promoters that can serve as regulatory regions for expression of heterologous nucleotide sequences of interest are needed for genetic manipulation of plants.

SUMMARY OF THE INVENTION

Compositions and methods for regulating expression of heterologous nucleotide sequences in a plant are provided. Compositions are novel nucleotide sequences for promoters that initiate transcription in a tissue-independent or constitutive manner, more particularly transcriptional initiation regions isolated from the plant genes Actin-2, Enolase, Gos-2 and L41. A method for expressing a heterologous nucleotide sequence in a plant using the transcriptional initiation sequences disclosed herein is provided. The method comprises transforming a plant cell with a transformation vector that comprises a heterologous nucleotide sequence operably linked to one of the plant promoters of the present invention and regenerating a stably transformed plant from the transformed plant cell. In this manner, the promoter sequences are useful for controlling the expression of operably linked coding sequences in a constitutive manner.

Downstream from and under the transcriptional initiation regulation of the promoter will be a sequence of interest that will provide for modification of the phenotype of the plant. Such modification includes modulating the production of an endogenous product, as to amount, relative distribution, or the like, or production of an exogenous expression product to provide for a novel function or product in the plant.

DETAILED DESCRIPTION OF THE INVENTION

Figure 1:
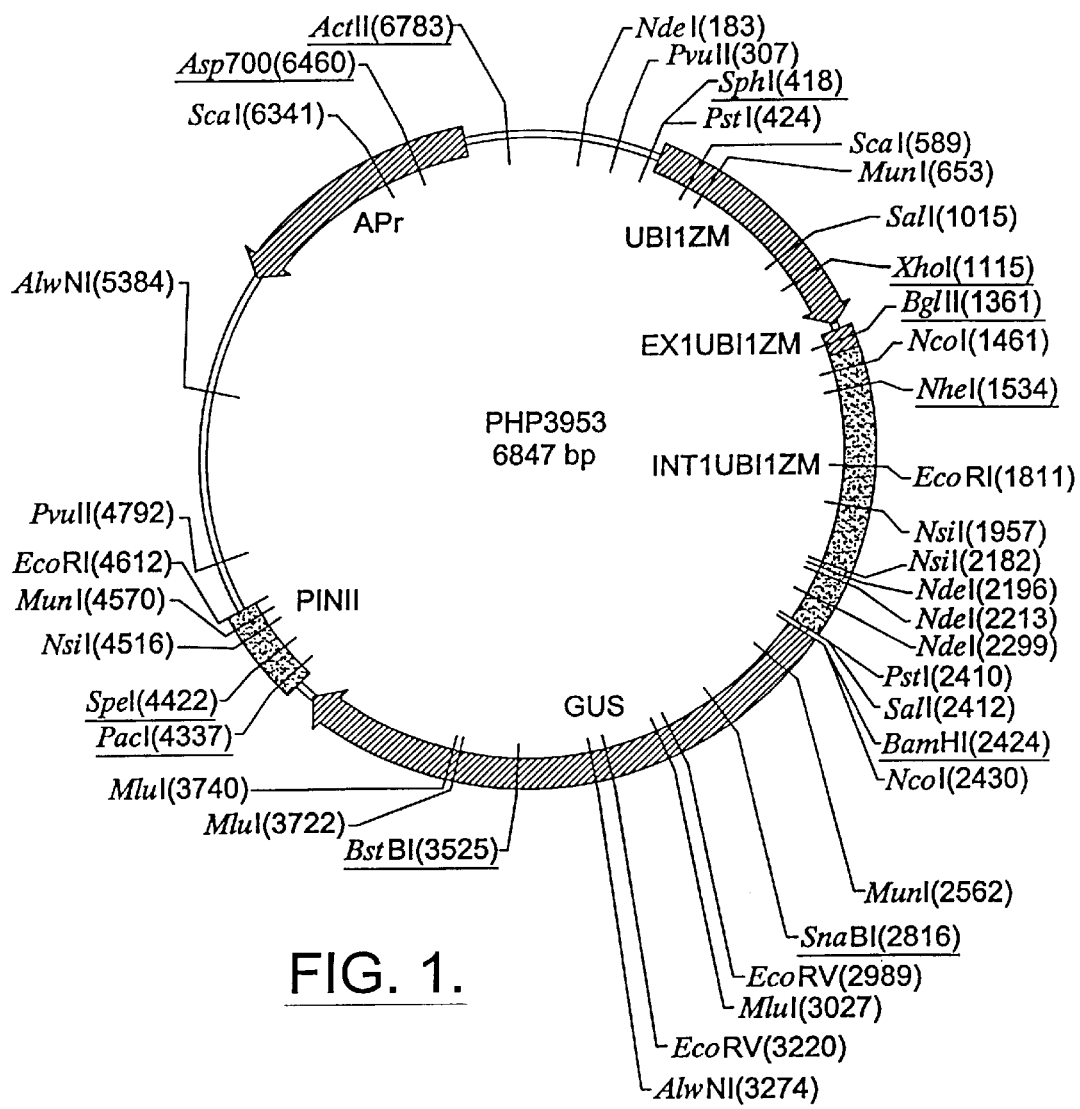
FIG. 1 shows the plasmid vector PHP3953 comprising the GUS gene operably linked to the ubiquitin promoter. Promoter fragments of the present invention were recloned into this plasmid in place of the ubiquitin promoter (UBI1ZM), with or without the ubiquitin 5' untranslated region (EX1UBI1ZM) and intron sequence (INT1UBI1ZM), and the resulting plasmid DNA was available in transformation studies to test promoter activity.
Figure 2:
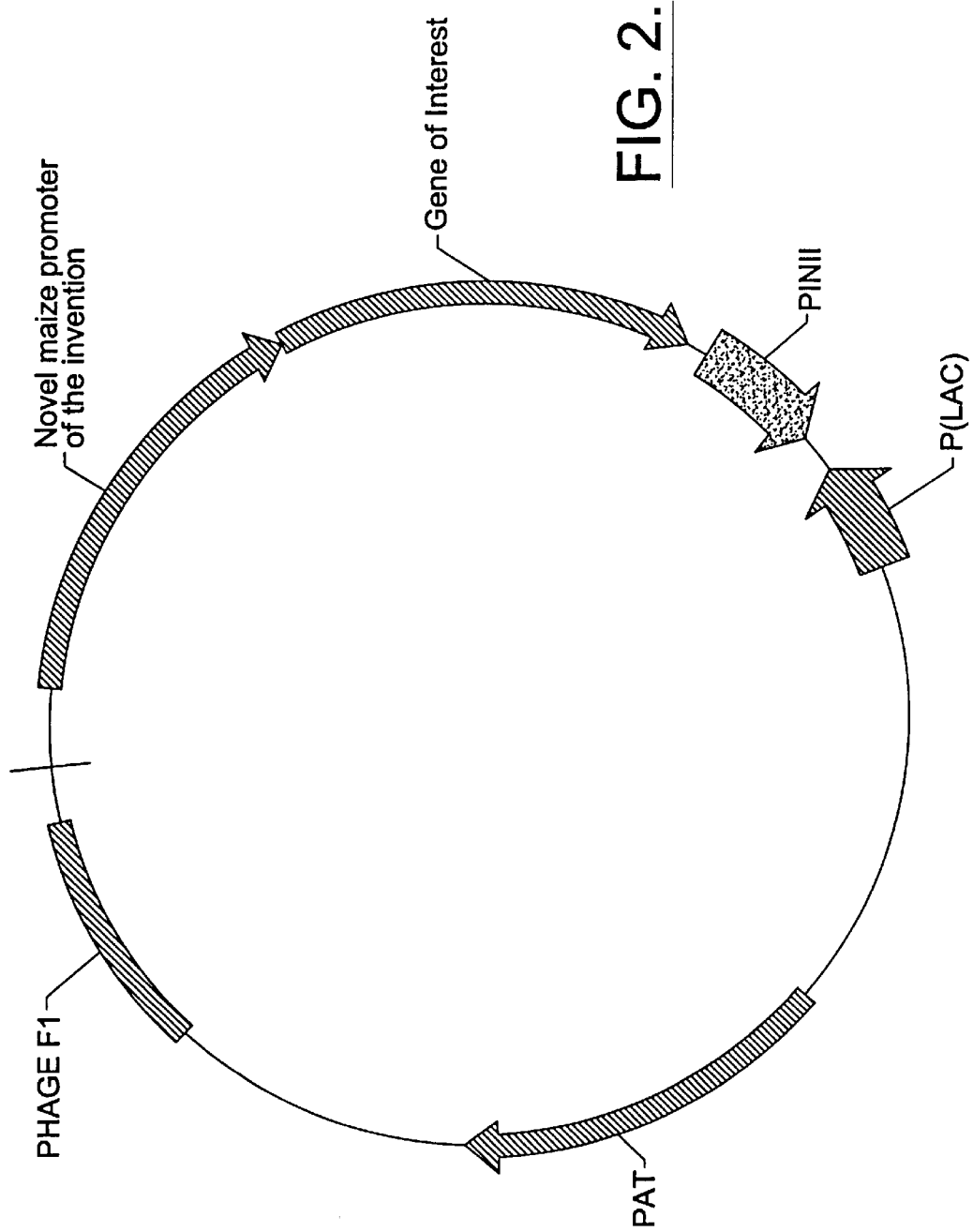
FIG. 2 schematically depicts an expression cassette for transformation, comprising a gene of interest operably linked to a promoter of the invention.
Figure 3:
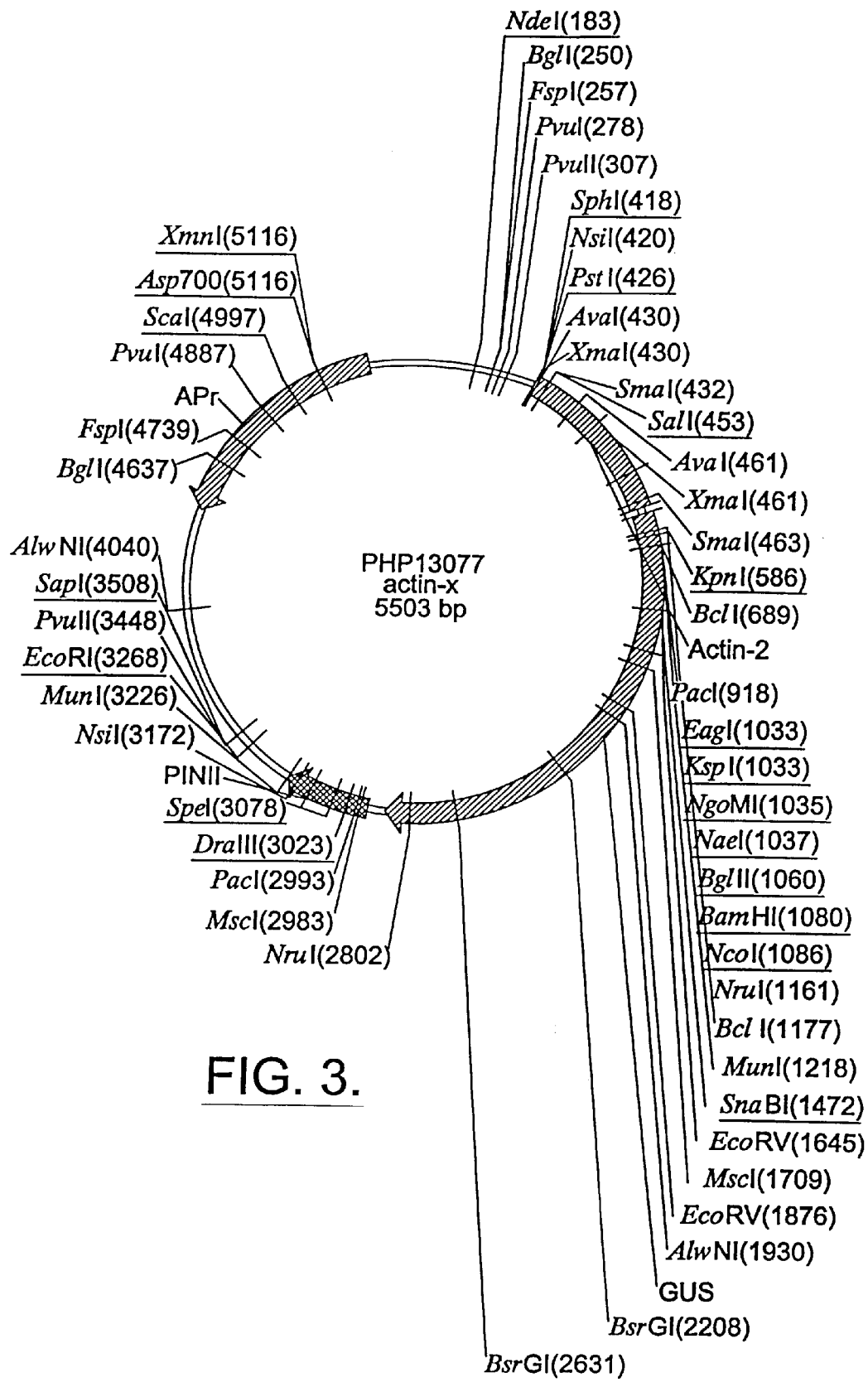
FIG. 3 schematically depicts a plasmid construct comprising the actin-2 promoter of the invention.
Figure 4:
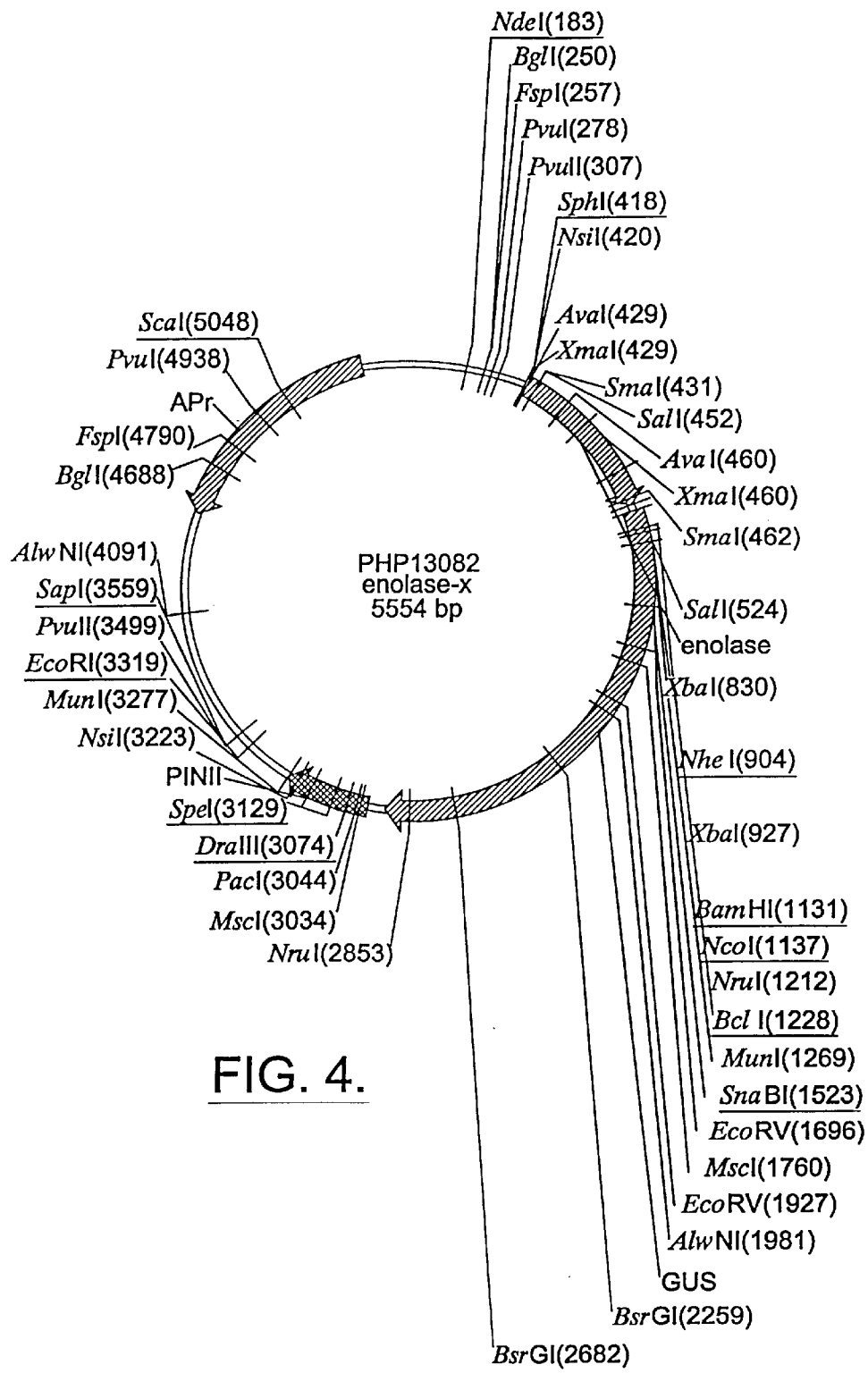
FIG. 4 schematically depicts a plasmid construct comprising the enolase promoter of the invention.
Figure 5:
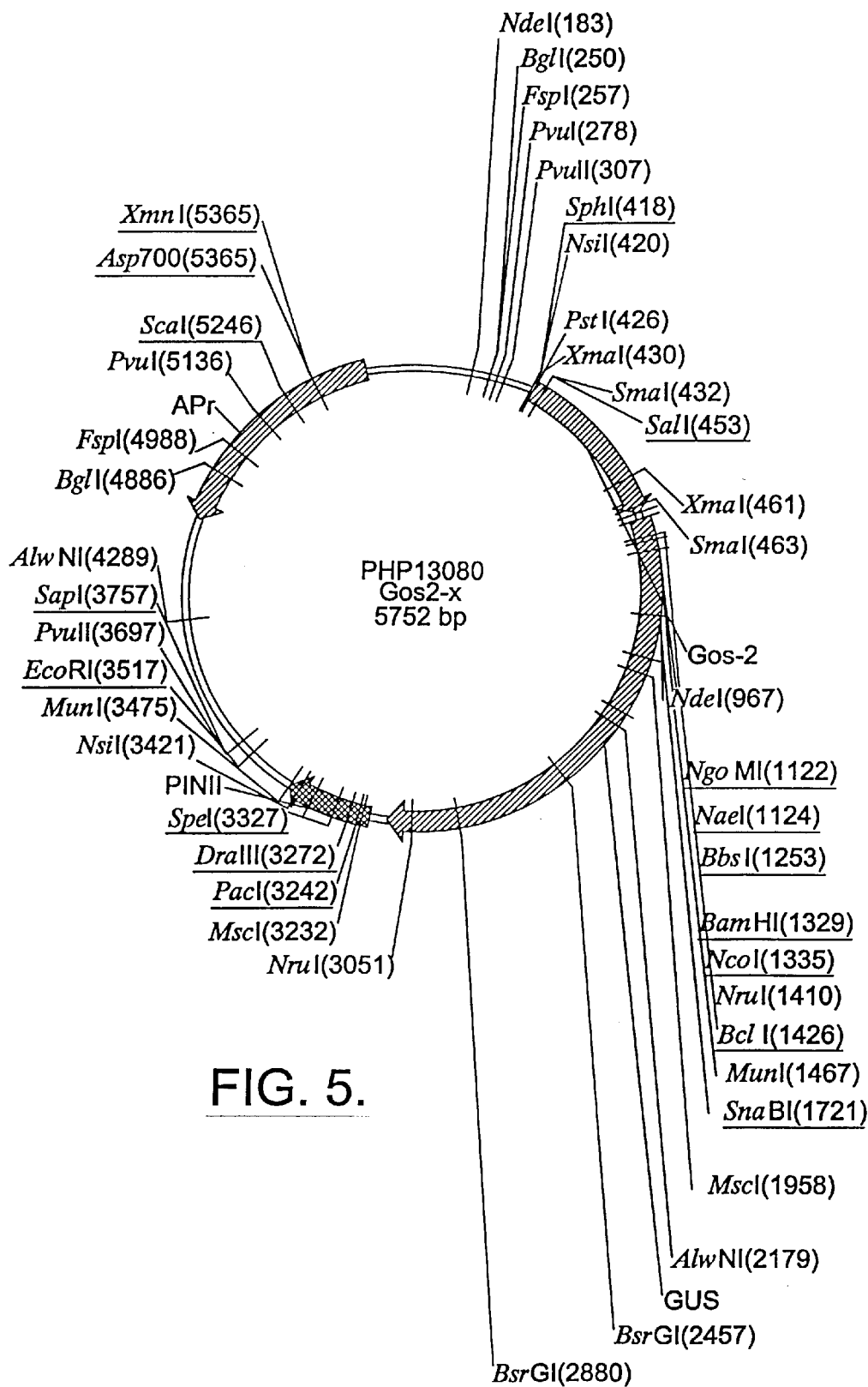
FIG. 5 schematically depicts a plasmid construct comprising the Gos-2 promoter of the invention.
Figure 6:
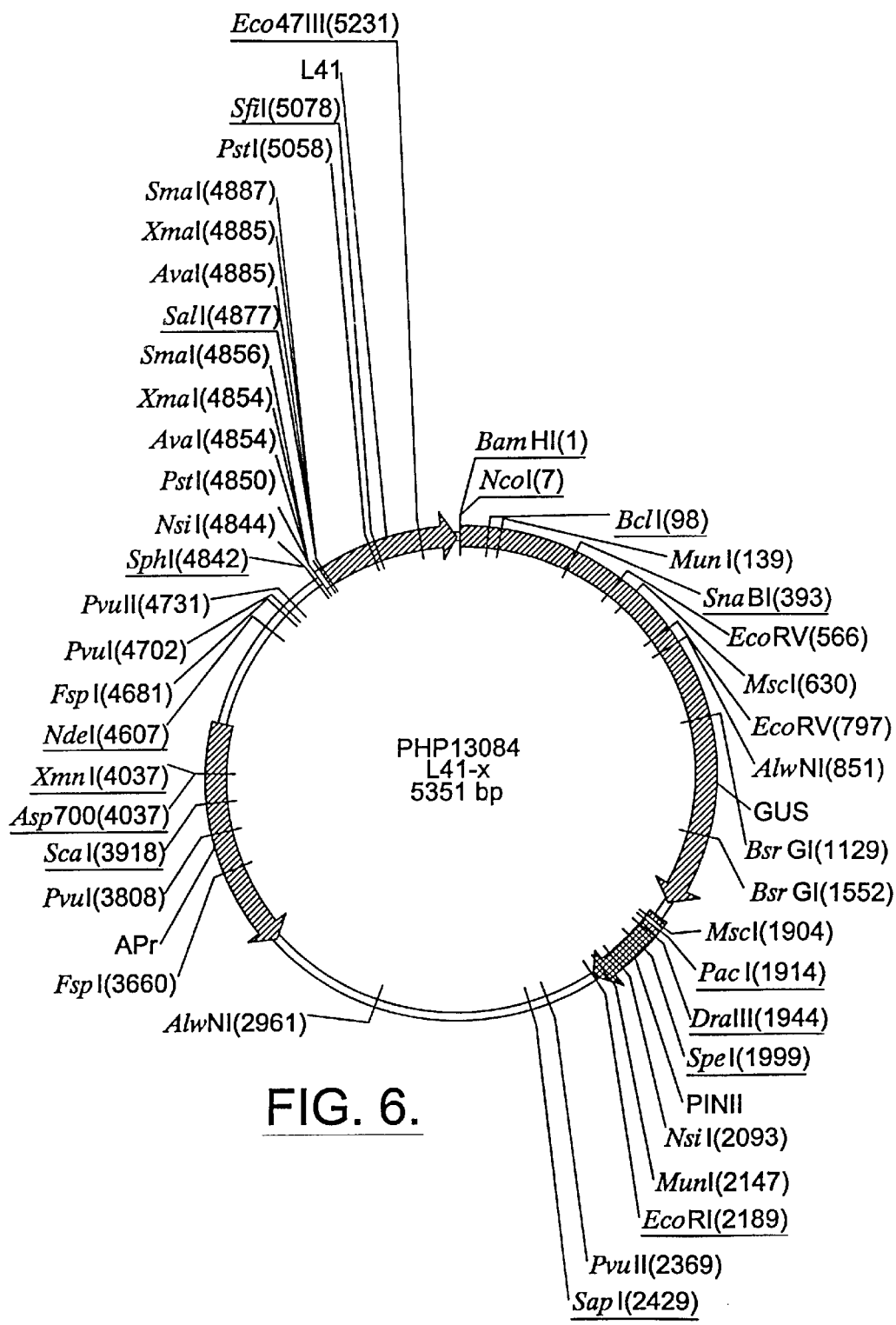
FIG. 6 schematically depicts a plasmid construct comprising the L-41 promoter of the invention.

In accordance with the present invention, nucleic acid constructs are provided that allow initiation of transcription in a "tissue-independent," "tissue-general," or "constitutive" manner. Constructs of the invention comprise regulated transcription initiation regions associated with protein translation elongation. Thus, the compositions of the present invention are drawn to novel nucleotide sequences for tissue-independent, tissue-general, or constitutive plant promoters. By "tissue-independent," "tissue-general," or "constitutive" is intended expression in the cells throughout a plant at most times and in most tissues. As with other promoters classified as "constitutive" (e.g. ubiquitin), some variation in absolute levels of expression can exist among different tissues or stages.

More particularly, the present invention provides for isolated nucleic acid molecules comprising nucleotide sequences for promoters of the genes actin-2, enolase, Gos-2 and L41. Actins are cytoskeletal proteins which are ubiquitous to nearly all eukaryotes. In plants, several forms of actin are expressed in a variety of tissues. SEQ ID NO:1 sets forth the nucleotide sequence for the promoter of one of these forms of actin which is present in maize. Enolase is an enzyme of the glycolytic pathway which catalyses the formation of phosphoenolpyruvate from 2-phophoglycerate. SEQ ID NO:2 sets forth the sequence of a maize enolase promoter. SEQ ID NO: 3 sets forth the sequence for the promoter of GOS-2. SEQ ID NO:4 sets forth the sequence for the promoter of L41. Based on BLAST searches of Genbank databases, L41 cDNA appears to encode a ribosomal protein. Northern blots of root, stem, leaf, ear shoot, kernel and tassie tissues showed mRNA from these genes expressed in many of the tissues.

The present invention provides for isolated nucleic acid molecules comprising the nucleotide sequences set forth in SEQ ID NOs:1–4, or the nucleotide sequences encoding the DNA sequences deposited in a bacterial host as Patent Deposit Nos: 203367, 203368, 203366, and 203369; and fragments and variants thereof.

Plasmid deposits comprising the promoters of the invention were made to the Patent Depository of American Type Culture Collection (ATCC) on Oct. 21, 1998, and assigned the Patent Deposit No: 203367 for plasmid PHP 13077 comprising the Actin-2 promoter, 203368 for plasmid PHP 13082 comprising the enolase promoter, 203366 for plasmid PHP 13080 comprising the Gos-2 promoter, and 203369 for plasmid PHP 13084 comprising the L41 promoter. FIGS. 3, 4, 5 and 6 schematically depict these plasmids. These deposits will be maintained under the terms of the Budapest Treaty on the International Recognition of the Deposit of Microorganisms for the purposes of Patent Procedure. These deposits were made merely as a convenience to those of skill in the art and are not an admission that a deposit is required under 35 U.S.C. §112.

The invention encompasses isolated or substantially purified nucleic acid compositions. An "isolated" or "purified" nucleic acid molecule, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

The promoter nucleotide sequences and methods disclosed herein are useful in regulating constitutive expression of any heterologous nucleotide sequence in a host plant in order to vary the phenotype of a plant.

Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497–502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,737,514; 5,723,756; 5,593,881; and Geiser et al. (1986) *Gene* 48:109); lectins (Van Damme et al. (1994) *Plant Mol. Biol.* 24:825); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837–5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

By "promoter" or "transcriptional initiation region" is intended a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Thus the promoter regions disclosed herein are generally further defined by comprising upstream regulatory elements such as enhancers and the like.

The regulatory sequences of the present invention, when operably linked to a heterologous nucleotide sequence of interest and inserted into a transformation vector, enable constitutive expression of the heterologous nucleotide sequence throughout the tissues of a plant stably transformed with this vector. That is the nucleotide sequence is expressed at most times and in most tissue types irrespective of developmental stage, environmental stress, and the like. By "heterologous nucleotide sequence" is intended a sequence that is not naturally occurring with the promoter sequence. While this nucleotide sequence is heterologous to the promoter sequence, it may be homologous, or native, or heterologous, or foreign, to the plant host.

It is recognized that the promoter sequences of the invention may be used to increase or decrease expression of nucleotide sequences that are native or homologous with respect to the promoter sequence. In this manner, the phenotype of the plant expressing the homologous sequences is altered.

It is also recognized that the nucleotide sequence operably linked to one of the promoter sequences disclosed herein may be an antisense sequence for a particular targeted gene of interest. Antisense constructions are complementary to at least a portion of the messenger RNA (mRNA) for the particular targeted gene, and are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used with the particular targeted gene sequences in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

The isolated promoter sequences of the present invention can be modified to provide for a range of constitutive expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-general, constitutive nature of expression may be changed. Generally, at least about 20 nucleotides of an isolated promoter sequence will be used to drive expression of a nucleotide sequence.

It is recognized that to increase transcription levels, enhancers may be utilized in combination with the promoter regions of the invention. Enhancers are nucleotide sequences that act to increase the expression of a promoter region. Enhancers are known in the art and include the SV40 enhancer region, the 35S enhancer element, and the like.

Modifications of the isolated promoter sequences of the present invention can provide for a range of constitutive expression of the heterologous nucleotide sequence. Thus, they may be modified to be weak constitutive promoters or strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

Fragments and variants of the disclosed nucleotide sequences are also encompassed by the present invention. By "fragment" is intended a portion of the nucleotide sequence. Fragments of a promoter nucleotide sequence may retain the biological activity and hence initiate and/or regulate expression. Alternatively, fragments of a nucleotide sequence that are useful as hybridization probes generally do not retain biological activity. Thus, fragments of a nucleotide sequence may range from at least about 20 nucleotides, about 50 nucleotides, about 100 nucleotides, and up to the full-length nucleotide sequence of the invention.

Thus, a fragment of the actin-2, enolase, Gos-2 and L41 promoter nucleotide sequences may encode a biologically active portion or it may be a fragment that can be used as a hybridization probe or PCR primer using methods disclosed below. A biologically active portion can be prepared by isolating a portion of one of the nucleotide sequences of the invention, and assessing the promoter activity of the portion. Nucleic acid molecules that are fragments of an actin-2, enolase, gos-2 and L41 promoter nucleotide sequence comprise at least 17, 20, 50, 75, 100, 150, 200, 250, 300, 350, 400, 450 nucleotides, or up to the number of nucleotides present in a full-length nucleotide sequence disclosed herein (for example, 613, 664, 862, and 461 nucleotides for SEQ ID NOs: 1, 2, 3, and 4 respectively.

By "variants" is intended substantially similar sequences. For nucleotide sequences, variants can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the invention will have at least 40%, 50%, 60%, 70%, generally at least 75%, 80%, 85%, preferably about 90% to 95% or more, and more preferably about 98% or more sequence identity to that particular nucleotide sequence as determined by sequence alignment programs described elsewhere herein using default parameters.

Variant nucleotide sequences also encompass sequences derived from a mutagenic and recombinogenic procedure such as DNA shuffling. With such a procedure, one or more of the promoter sequences disclosed herein can be manipulated to create a new promoter sequence possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire actin-2, enolase, Gos-2 or L41 promoter sequences set forth herein, or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the promoter sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire actin-2, enolase, Gos-2 or L41 promoter sequence disclosed herein, or one or more portions thereof, may be used as a probe capable of specifically hybridizing to corresponding actin-2, enolase, Gos-2 or L41 sequences. To achieve specific hybridization under a variety of conditions, such probes include sequences that are unique among e promoter sequences and are preferably at least about 10 nucleotides in length, and most preferably at least about 20 nucleotides in length. Such probes may be used to amplify corresponding plant sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m$=81.5° C.+16.6(log M)+0.41(%GC)−0.61(% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology— Hybridization with Nucleic Acid Probes,* Part I, Chapter 2 (Elsevier, N.Y.); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that have promoter activity and which hybridize under stringent conditions to the promoter sequences disclosed herein, or to fragments thereof, are encompassed by the present invention. Such sequences will be at least 40% to 50% homologous, about 60% to 70% homologous, and even about 75%, 80%, 85%, 90%, 95% to 98% homologous or more with the disclosed sequences. That is, the sequence identity of sequences may range, sharing at least 40% to 50%, about 60% to 70%, and even about 75%, 80%, 85%, 90%, 95% to 98% or more sequence identity. The promoter regions of the invention may be used to isolate substantially identical sequences from any plant species, including but not limited to any plant species described herein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad Sci.* 85:2444–2448; the algorithm of Karlin and Altschul (1990) *Proc. Natl. Acad Sci. USA* 872264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. The BLAST programs of Altschul et at (1990) *J. Mol. Biol.* 215:403 are based on the algorithm of Karlin and Altschul (1990) supra. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See information available at the URL www.ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The nucleotide sequences for the constitutive promoters disclosed in the present invention, as well as variants and fragments thereof, are useful in the genetic manipulation of any plant when operably linked with a nucleotide sequence whose constitutive expression is to be controlled to achieve a desired phenotypic response. By "operably linked" is intended the transcription or translation of the heterologous nucleotide sequence is under the influence of the promoter sequence. In this manner, the nucleotide sequences for the promoters of the invention may be provided in expression cassettes along with nucleotide sequences of interest for expression in the plant of interest.

Such expression cassettes will comprise a transcriptional initiation region comprising one of the promoter nucleotide sequences of the present invention, or variants or fragments thereof, operably linked to the nucleotide sequence whose expression is to be controlled by the constitutive promoters disclosed herein. Such an expression cassette is provided with a plurality of restriction sites for insertion of the nucleotide sequence to be under the transcriptional regulation of the regulatory regions. The expression cassette may additionally contain selectable marker genes.

The transcriptional cassette will include in the 5'-to-3' direction of transcription, a transcriptional and translational initiation region, a heterologous nucleotide sequence of interest, and a transcriptional and translational termination region functional in plants. The termination region may be native with the transcriptional initiation region comprising one of the promoter nucleotide sequences of the present invention, may be native with the DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; Joshi heterologous et al. (1987) Nucleic Acid Res. 15:9627–9639.

The expression cassette comprising the promoter sequence of the present invention operably linked to a nucleotide sequence may also contain at least one additional nucleotide sequence for a gene to be cotransformed into the organism. Alternatively, the additional sequence(s) can be provided on another expression cassette.

Where appropriate, the heterologous nucleotide sequence whose expression is to be under the control of the promoter sequence of the present invention and any additional nucleotide sequence(s) may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus) (Allison et al. (1986)); MDMV leader (Maize Dwarf Mosaic Virus) (*Virology* 154:9–20); human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) *Molecular Biology of RNA*, pages 237–256); and maize chlorotic mottle virus leader (MCMV) (Lommel et al. (1991) *Virology* 81:382–385). See also Della-Cioppa et al. (1987) *Plant Physiology* 84:965–968. Other methods known to enhance translation and/or mRNA stability can also be utilized, for example, introns, and the like.

In those instances where it is desirable to have the constitutively expressed product of the heterologous nucleotide sequence directed to a particular organelle, such as the chloroplast or mitochondrion, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

The promoters may be used to drive reporter genes and/or selectable marker genes. Examples of suitable reporter genes known in the art can be found in, for example, Jefferson et al. (1991) in *Plant Molecular Biology Manual*, ed. Gelvin et al. (Kluwer Academic Publishers), pp. 1–33; DeWet et al. (1987) *Mol Cell. Biol.* 7:725–737; Goff et al. (1990) *EMBO J.* 9:2517–2522; Kain et al. (1995) *BioTechniques* 19:650–655; and Chiu et al. (1996) *Current Biology* 6:325:330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) i EMBO J. 2:987–992); methotrexate (Herrera Estrella et al. (1983) *Nature* 303:209–213; Meijer et al. (1991) *Plant Mol. Biol.* 16:807–820); hygromycin (Waldron et al. (1985) *Plant Mol. Biol* 5:103–108; Zhijian et al. (1995) *Plant Science* 108:219–227); streptomycin (Jones et al. (1987) *Mol Gen. Genet.* 210:86–91); spectinomycin (Bretagne-Sagnard et al. (1996) *Transgenic Res.* 5:131–137); bleomycin (Hille et al. (1990) *Plant Mol. Biol.* 7:171–176); sufonamide (Guerineau et al. (1990) *Plant Mol. Biol* 15:127–136); bromoxynil (Stalker et al. (1988) *Science* 242:419–423); glyphosate (Shaw et al. (1986) *Science* 233:478–481); phosphinothricin (DeBlock et al. (1987) *EMBO J.* 6:2513–2518).

Other genes that could serve utility in the recovery of transgenic events but might not be required in the final product would include, but are not limited to, examples such as GUS (b-glucoronidase; Jefferson (1987) *Plant Mol. Biol.*

Rep. 5:387), GFP (green florescence protein; Chalfie et al. (1994) Science 263:802), luciferase (Riggs et al. (1987) Nucleic Acid Res. 15(19):8115; Luehrsen et al. (1992) Methods Enzymol. 216:397–414) and the maize genes encoding for anthocyanin production (Ludwig et al. (1990) Science 247:449).

The expression cassette comprising the particular promoter sequence of the present invention operably linked to a nucleotide sequence of interest can be used to transform any plant. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) Biotechniques 4:320–334), electroporation (Riggs et al. (1986) Proc. Natl. Acad. Sci. USA 83:5602–5606, Agrobacterium-mediated transformation (Townsend et al., U.S. Pat. No. 5,563,055), direct gene transfer (Paszkowski et al. (1984) EMBO J. 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U. S. Pat. No. 5,932,782; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Biotechnology 6:923–926). Also see Weissinger et al. (1988) Ann. Rev. Genet. 22:421–477; Sanford et al. (1987) Particulate Science and Technology 5:27–37 (onion); Christou et al. (1988) Plant Physiol. 87:671–674 (soybean); McCabe et al. (1988) Bio/Technology 6:923–926 (soybean); Finer and McMullen (1991) In Vitro Cell Dev. Biol 27P: 175–182 (soybean); Singh et al. (1998) Theor. Appl. Genet. 96:319–324 (soybean); Datta et al. (1990) Biotechnology 8:736–740 (rice); Klein et al. (1988) Proc. Natl. Acad. Sci. USA 85:4305–4309 (maize); Klein et al. (1988) Biotechnology 6:559–563 (maize); Tomes, U.S. Pat. No. 5,240,855; Buising et al., U. S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91:440–444 (maize); Fromm et al. (1990) Biotechnology 8:833–839 (maize); Hooykaas-Van Slogteren et al. (1984) Nature (London) 311:763–764; Bowen et al., U.S. Pat. No. 5,736,369 (cereals); Bytebier et al. (1987) Proc. Natl. Acad Sci. USA 84:5345–5349 (Liliaceae); De Wet et al. (1985) in The Experimental Manipulation of Ovule Tissues, ed. Chapman et al. (Longman, New York), pp. 197–209 (pollen); Kaeppler et al. (1990) Plant Cell Reports 9:415–418 and Kaeppler et al. (1992) Theor. Appl. Genet. 84:560–566 (whisker-mediated transformation); D Halluin et al. (1992) Plant Cell 4:1495–1505 (electroporation); Li et al. (1993) Plant Cell Reports 12:250–255 and Christou and Ford (1995) Annals of Botany 75:407–413 (rice); Osjoda et al. (1996) Nature Biotechnology 14:745–750 (maize via Agrobacterium tumefaciens); all of which are herein incorporated by reference.

The cells that have been transformed may be grown into plants in accordance with conventional ways. See, for example, McCormick et al. (1986) Plant Cell Reports 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The present invention may be used for transformation of any plant species, including, but not limited to, corn (Zea mays), Brassica sp. (e.g., B. napus, B. rapa, B. juncea), particularly those Brassica species useful as sources of seed oil, alfalfa (Medicago sativa), rice (Oryza sativa), rye (Secale cereale), sorghum (Sorghum bicolor, Sorghum vulgare), millet (e.g., pearl millet (Pennisetum glaucum), proso millet (Panicum miliaceum), foxtail millet (Setaria italica), finger millet (Eleusine coracana)), sunflower (Helianthus annuus), safflower (Carthamus tinctorius), wheat (Triticum aestivum), soybean (Glycine max), tobacco (Nicotiana tabacum), potato (Solanum tuberosum), peanuts (Arachis hypogaea), cotton (Gossypium barbadense, Gossypium hirsutum), sweet potato (Ipomoea batatus), cassava (Manihot esculenta), coffee (Cofea spp.), coconut (Cocos nucifera), pineapple (Ananas comosus), citrus trees (Citrus spp.), cocoa (Theobroma cacao), tea (Camellia sinensis), banana (Musa spp.), avocado (Persea americana), fig (Ficus casica), guava (Psidium guajava), mango (Mangifera indica), olive (Olea europaea), papaya (Carica papaya), cashew (Anacardium occidentale), macadamia (Macadamia integrifolia), almond (Prunus amygdalus), sugar beets (Beta vulgaris), sugarcane (Saccharum spp.), oats, barley, vegetables, ornamentals, and conifers.

Vegetables include tomatoes (Lycopersicon esculentum), lettuce (e.g., Lactuca saliva), green beans (Phaseolus vulgaris), lima beans (Phaseolus limensis), peas (Lathyrus spp.), and members of the genus Cucumis such as cucumber (C. sativus), cantaloupe (C. cantalupensis), and musk melon (C. melo). Ornamentals include azalea (Rhododendron spp.), hydrangea (Macrophylla hydrangea), hibiscus (Hibiscus rosasanensis), roses (Rosa spp.), tulips (Tulipa spp.), daffodils (Narcissus spp.), petunias (Petunia hybrida), carnation (Dianthus caryophyllus), poinsettia (Euphorbia pulcherrima), and chrysanthemum. Conifers that may be employed in practicing the present invention include, for example, pines such as loblolly pine (Pinus taeda), slash pine (Pinus elliotii), ponderosa pine (Pinus ponderosa), lodgepole pine (Pinus contorta), and Monterey pine (Pinus radiata); Douglas-fir (Pseudotsuga menziesii); Western hemlock (Tsuga canadensis); Sitka spruce (Picea glauca); redwood (Sequoia sempervirens); true firs such as silver fir (Abies amabilis) and balsam fir (Abies balsamea); and cedars such as Western red cedar (Thuja plicata) and Alaska yellow-cedar (Chamaecyparis nootkatensis). Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

The following examples are offered by way of illustration and not by way of limitation.

Experimental

Promoter regions for the maize genes actin-2, enolase, Gos-2 and L41 were isolated from maize plants and cloned. The sequences for these promoters are set forth in SEQ ID NOs: 1, 2, 3 and 4 respectively. The method for their isolation is described below.

Example 1
Isolation and Cloning of the Promoters

Pioneer-proprietary maize EST (expressed sequence tag) library was examined by computer and manually to identify candidate genes of frequency among the various entries and distribution among maize tissues so as to be likely expressed ubiquitously (or nearly so) in maize and at relatively high mRNA levels. Approximately ten candidate genes were so identified. Northern blots were run with various maize tissue mRNA samples, probed with these ESTs. Those ESTs yielding apparently good mRNA expression were selected for cloning of the corresponding promoter fragments. The putative promoters were isolated from genomic maize DNA according to methods and materials provided in the Genome Walker Kit by Clontech Corporation, and as described in more detail below. Four of these putative promoters were cloned upstream of a GUS reporter cDNA (PHP3953, FIG. 1). For each of these promoters, two types of constructs were generated, one with and the other without the maize ubiquitin 5'UT (EX1UBI1ZM) and intron sequence (INT1UBI1ZM of PHP3953).

This plus/minus INT1UBI1ZM sequence was to allow testing for whether that ubi sequence significantly aided the transcriptional activity of the promoters. The constructs are used to test transient and stable maize transformation, with scoring of GUS expression levels, temporally and developmentally relative to the parent PHP3953 construct which contains the maize Ubiquitin promoter/ intron/ and GUS reporter (FIG. 1), and to a basal construct containing only the GUS reporter.

The procedure for promoter isolation is described in the user manual for the Genome Walker kit sold by Clontech Laboratories, Inc., Palo Alto, Calif. Genomic DNA libraries of line B73 were constructed by digesting the maize genomic DNA with 5 different enzymes DraI, Eco RV, PvuII, ScaI and StuI. The resulting DNA is referred to as DL1–DL5, respectively. For isolation of specific promoter regions, two non-overlapping gene-specific primers were designed from the sequences of abundant ESTs in the Pioneer/HGS database. The primers were designed to amplify the region upstream of the coding sequence, i.e. the 5'-untranslated region and promoter region of the chosen gene. The sequences of the primers are given below for each promoter described. The first round of PCR was performed on each DNA sample (DL1–5) with SEQ ID NO:18 the Clontech Primer AP1 (sequence 5' -gtaatacgactcactatagggc-3'), and the gene-specific primer (gsp1) with the following sequences:

Actin-2 gsp1: 5' -cttggactgggcctcgtcaccaacata-3' (SEQ ID NO:5)

Gos-2 gsp1: 5' -accagcaccagagtcctcagcatttgcctcag-3' (SEQ ID NO:6)

Enolase gsp1: 5' -tttgcctcgcaagtcacgctcgattcgg-3' (SEQ ID NO:7)

L41 gsp1: 5' -tttccctgggcagacaggctatccttacc-3' (SEQ ID NO:8)

PCR was performed in a 2400 Thermal Cycler with heated lid from Perkin Elmer (Foster City, Calif.) using reagents supplied with the Genome Walker kit. The following cycling parameters were used: seven cycles of 94° C. for 2 sec., then 72° C. for 3 min., followed by 32 cycles of 94° C. for 2 sec., 67° C. for 3 min. Finally, the samples were held at 67° C. for 4 min., then at 4° C. until analyzed.

As described in the user manual, the DNA from the first round of PCR was then diluted and used as a template in a second round of PCR using SEQ ID NO:19, the Clontech AP2 primer (sequence 5'- actatagggcacgcgtggt-3'), and gene specific primer gsp2 with the following sequences:

Actin-2 gsp2: 5' -actgatgatgccggagatctaggagaag-3' (SEQ ID NO:9)

Gos-2 gsp2: 5' -tcgctttcctggaggaggcgtggagcgcac-3' (SEQ ID NO:10)

Enolase gsp2: 5' -ccacttggcggtgacagatgttcgagc-3' (SEQ ID NO:11)

L41 gsp2: 5'-cttggtcttaggaacgttcaccattttggcgg-3' (SEQ ID NO:12)

The cycling parameters for the second round were: five cycles of 94° C. for 2 sec., then 72° C. for 3 min., followed by 20 cycles of 94° C. for 2 sec., and 67° C. for 3 min., finally four min. at 67° C. and then held at 4° C. Approximately ten μl of each reaction were run on a 1% agarose gel, and bands larger than 500 bp were excised, purified with Wizard PCR Prep Kit (Promega, Madison, Wis.) and cloned into the TA vector pCR 2.1 (Invitrogen, San Diego, Calif.). Clones were sequenced for verification, and then 2 μl was amplified with gene specific primer gsp3 (sequence below) and the adapter primer AP3 to add recognition sequences for restriction enzymes to ease the cloning process. This amplification was according to the following cycling parameters: five cycles of 94° C. for 2 sec., 46° C. for 30 sec., 72° C. for 3 min., followed by 20 cycles of 94° C. for 2 sec., 67° C. for 3 min., finally 67° C. for 4 min., and held at 4° C.

AP3: 5' -atatgcatgcatctgcagatcccgggactatagggcacgcgtggt-3' (SEQ ID NO:13)

Acti-2 Gsp3: 5' -atccatggtgtcgtgtggatccactgatgatgccggagatctagg-3' (SEQ ID NO:14)

Gos-2 Gsp3: 5' -atccatggtgtcgtgtggatcctcgctttcctggaggaggcgtg-3' (SEQ ID NO:15)

Enolase Gsp3: 5' -atccatggtgtcgtgtggatcccacttggcggtgacagatgttc-3' (SEQ ID NO:16)

L41 Gsp3: 5' -atccatggtgtcgtgtggatcccttggtcttaggaacgttcacca-3' (SEQ ID NO:17)

Ten ul of the resulting amplified DNA was run on a 1% agarose gel, purified with Wizard PCR Prep Kit and digested with SphI and BamHI, run on gel, purified, then subcloned into PHP3953 cut with SphI and BglII, thereby substituting the ubiquitin promoter. Final sequences were determined for the resulting plasmids, the pertinent parts of which are set forth in SEQ ID NOs: 1–4. The sequences of these four promoters showed no significant match to other transcriptional promoters when checked by GCG BlastN analyses of the GeneSeqN database. The GeneSeq database is published by Derwent Scientific Publications and distributed electronically by Oxford Molecular Group. Oxford Molecular coordinates the content assembly of the GeneSeq database with Derwent. The GeneSeq database is compiled for institutional and corporate use by GCG, which is also now a part of Oxford Molecular.

Example 2
Expression Using Novel Maize Promoters

A transient expression assay is used to test the cloned DNAs for promoter activity. The promoter sequences of SEQ ID NOs:1–4 were cloned into a GUS expression vector (FIG. 1) as described above in Example 1.

Plasmid DNA was bombarded into maize cell suspension culture and GUS activity is measured, using the ubiquitin promoter as a control, by counting blue spots after staining for GUS activity as described in Jefferson (1987) *Plant Mol. Biol. Rep.* 5:387–405.

Example 3
Transformation and Regeneration of Transgenic Plants

Immature maize embryos from greenhouse donor plants are bombarded with a plasmid containing an actin-2, enolase, Gos-2 or L41 promoter of the invention operably linked to a gene of interest plus a plasmid containing the selectable marker gene PAT (Wohlleben et al. (1988) *Gene* 70:25–37) that confers resistance to the herbicide Bialaphos. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the gene of interest operably linked to an actin-2, enolase, Gos-2 or L41 promoter of the invention (SEQ ID NOs: 1–4 respectively) is made. The respective constructs comprising these promoters are shown in FIGS. 3, 4, 5, and 6. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in TrisEDTA buffer (1 μg total)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for expression and/or activity of the gene of interest.

APPENDIX
272 V

| Ingredient | Amount | Unit |
|---|---|---|
| D-I $H_2O$ | 950.000 | Ml |
| MS Salts (GIBCO 11117-074) | 4.300 | G |
| Myo-Inositol | 0.100 | G |
| MS Vitamins Stock Solution ## | 5.000 | Ml |
| Sucrose | 40.000 | G |
| Bacto-Agar @ | 6.000 | G |

Directions

@=Add after bringing up to volume
  Dissolve ingredients in polished D-I $H_2O$ in sequence
  Adjust to pH 5.6
  Bring up to volume with polished D-I $H_2O$ after adjusting pH
  Sterilize and cool to 60° C.
=Dissolve 0.100 g of Nicotinic Acid; 0.020 g of Thiamine.HCL; 0.100 g of Pyridoxine HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.
Total Volume (L)=1.00

288 J

| Ingredient | Amount | Unit |
|---|---|---|
| D-I $H_2O$ | 950.000 | Ml |
| MS Salts | 4.300 | G |
| Myo-Inositol | 0.100 | G |
| MS Vitamins Stock Solution ## | 5.000 | Ml |
| Zeatin .5 mg/ml | 1.000 | Ml |
| Sucrose | 60.000 | G |
| Gelrite @ | 3.000 | G |
| Indoleacetic Acid 0.5 mg/ml # | 2.000 | Ml |
| 0.1 mM Abscisic Acid | 1.000 | Ml |
| Bialaphos 1 mg/ml # | 3.000 | Ml |

Directions

@=Add after bringing up to volume
  Dissolve ingredients in polished D-I $H_2O$ in sequence
  Adjust to pH 5.6
  Bring up to volume with polished D-I $H_2O$ after adjusting pH
  Sterilize and cool to 60° C.
  Add 3.5 g/L of Gelrite for cell biology.

=Dissolve 0.100 g of Nicotinic Acid; 0.020 g of Thiamine.HCL; 0.100 g of Pyridoxine.HCL; and 0.400 g of Glycine in 875.00 ml of polished D-I H$_2$O in sequence. Bring up to volume with polished D-I H$_2$O. Make in 400 ml portions. Thiamine.HCL & Pyridoxine.HCL are in Dark Desiccator. Store for one month, unless contamination or precipitation occurs, then make fresh stock.

Total Volume (L)=1.00

| 560 R | | |
|---|---|---|
| Ingredient | Amount | Unit |
| D-I Water, Filtered | 950.000 | Ml |
| CHU (N6) Basal Salts (SIGMA C-1416) | 4.000 | G |
| Eriksson's Vitamin Mix (1000X SIGMA-1511 | 1.000 | Ml |
| Thiamine.HCL 0.4 mg/ml | 1.250 | Ml |
| Sucrose | 30.000 | G |
| 2,4-D 0.5 mg/ml | 4.000 | Ml |
| Gelrite @ | 3.000 | G |
| Silver Nitrate 2 mg/ml # | 0.425 | Ml |
| Bialaphos 1 mg/ml # | 3.000 | Ml |

Directions

@=Add after bringing up to volume
=Add after sterilizing and cooling to temp.

Dissolve ingredients in D-I H$_2$O in sequence

Adjust to pH 5.8 with KOH

Bring up to volume with D-I H$_2$O

Sterilize and cool to room temp.

Total Volume (L)=1.00

| 560 Y | | |
|---|---|---|
| Ingredient | Amount | Unit |
| D-I Water, Filtered | 950.000 | Ml |
| CHU (N6) Basal Salts (SIGMA C-1416) | 4.000 | G |
| Eriksson's Vitamin Mix (1000X SIGMA-1511 | 1.000 | Ml |
| Thiamine.HCL 0.4 mg/ml | 1.250 | Ml |
| Sucrose | 120.000 | G |
| 2,4-D 0.5 mg/ml | 2.000 | Ml |
| L-Proline | 2.880 | G |
| Gelrite @ | 2.000 | G |
| Silver Nitrate 2 mg/ml # | 4.250 | Ml |

Directions

@=Add after bringing up to volume
=Add after sterilizing and cooling to temp.

Dissolve ingredients in D-I H$_2$O in sequence

Adjust to pH 5.8 with KOH

Bring up to volume with D-I H$_2$O

Sterilize and cool to room temp.

Autoclave less time because of increased sucrose

Total Volume (L)=1.00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated promoter that drives expression, said promoter comprising the nucleotide sequence set forth in SEQ ID NO:3.

2. An expression cassette comprising a promoter and a first nucleotide sequence operably linked to said promoter, wherein said promoter drives expression of said first nucleotide sequence in a plant cell and wherein said promoter comprises a second nucleotide sequence which is the entire nucleotide sequence set forth in SEQ ID NO:3.

3. A transformed plant cell having stably incorporated into its genome an expression cassette comprising a promoter and a first nucleotide sequence operably linked to said promoter, wherein said promoter drives expression of said first nucleotide sequence in a plant cell and wherein said promoter comprises a second nucleotide sequence which is the entire nucleotide sequence set forth in SEQ ID NO:3.

4. A transformed plant having stably incorporated into its genome an expression cassette comprising a promoter and a first nucleotide sequence operably linked to said promoter, wherein said promoter drives expression of said first nucleotide sequence in a plant cell and wherein said promoter comprises a second nucleotide sequence which is the entire nucleotide sequence set forth in SEQ ID NO:3.

5. A method for expressing a first nucleotide sequence in a plant cell, said method comprising transforming a plant cell with a transformation vector comprising an expression cassette, said expression cassette comprising said first nucleotide sequence and a promoter operably linked to said first nucleotide sequence, wherein said promoter drives expression of said first nucleotide sequence in a plant cell and wherein said promoter comprises a second nucleotide sequence which is the entire nucleotide sequence set forth in SEQ ID NO:3.

6. A method for expressing a nucleotide sequence in a plant, said method comprising transforming a plant cell according to the method set forth in claim 5, and further comprising regenerating a transformed plant from said plant cell, wherein said plant has stably incorporated into its genome said expression cassette.

7. An isolated promoter that drives expression, said promoter comprising a fragment of the nucleotide sequence set forth in SEQ ID NO:3, wherein said fragment retains promoter activity.

8. An expression cassette comprising a promoter and a first nucleotide sequence operably linked to said promoter, wherein said promoter drives expression of said first nucleotide sequence in a plant cell and wherein said promoter comprises a second nucleotide sequence which is a fragment of the nucleotide sequence set forth in SEQ ID NO:3, wherein said fragment retains promoter activity.

9. A transformation vector comprising the expression cassette of claim 8.

10. A transformed plant cell having stably incorporated into its genome an expression cassette comprising a promoter and a first nucleotide sequence operably linked to said promoter, wherein said promoter drives expression of said first nucleotide sequence in a plant cell and wherein said promoter comprises a second nucleotide sequence which is a fragment of the nucleotide sequence set forth in SEQ ID NO:3, wherein said fragment retains promoter activity.

11. A transformed plant having stably incorporated into its genome an expression cassette comprising a promoter and a first nucleotide sequence operably linked to said promoter, wherein said promoter drives expression of said first nucleotide sequence in a plant cell and wherein said promoter comprises a second nucleotide sequence which is a fragment of the nucleotide sequence set forth in SEQ ID NO:3, wherein said fragment retains promoter activity.

12. The plant of claim 11, wherein said plant is a monocot.

13. The plant of claim 12, wherein said monocot is maize.

14. The plant of claim 11, wherein said plant is a dicot.

15. Transformed seed of the plant of claim 11.

16. The plant of claim 11, wherein said promoter is a maize promoter.

17. A method for expressing a first nucleotide sequence in a plant cell, said method comprising transforming a plant cell with a transformation vector comprising an expression cassette, said expression cassette comprising said first nucleotide sequence and a promoter operably linked to said first nucleotide sequence, wherein said promoter drives expression of said first nucleotide sequence in a plant cell and wherein said promoter comprises a second nucleotide sequence which is a fragment of the nucleotide sequence set forth in SEQ ID NO:3, wherein said fragment retains promoter activity.

18. A method for expressing a nucleotide sequence in a plant, said method comprising transforming a plant cell according to the method set forth in claim 17, and further comprising regenerating a transformed plant from said plant cell, wherein said plant has stably incorporated into its genome said expression cassette.

* * * * *